United States Patent [19]
Hall et al.

[11] Patent Number: 5,207,389
[45] Date of Patent: May 4, 1993

[54] CELLULOSIC CARRIER

[75] Inventors: Glenn E. Hall, Maumee; Daniel R. Kory, Toledo, both of Ohio

[73] Assignee: The Andersons, Maumee, Ohio

[21] Appl. No.: 908,055

[22] Filed: Jul. 6, 1992

[51] Int. Cl.$^5$ ............................................. B02C 19/12
[52] U.S. Cl. .......................................... 241/3; 241/21; 241/24; 241/28
[58] Field of Search .................... 241/3, 21, 24, 28, 18

[56] References Cited

U.S. PATENT DOCUMENTS

| | | | |
|---|---|---|---|
| 453,364 | 6/1891 | Taylor | 241/9 X |
| 3,658,613 | 4/1972 | Steiger | 241/28 X |
| 3,993,498 | 11/1976 | Koekemoer | 241/3 X |
| 4,053,112 | 10/1977 | Vander Hooven . | |
| 4,563,344 | 1/1986 | Kotz et al. . | |
| 4,578,147 | 3/1986 | Lindah et al. | 241/21 X |
| 4,757,948 | 7/1988 | Nonaka et al. | 241/9 X |
| 5,041,410 | 8/1991 | Ivie . | |
| 5,062,954 | 11/1991 | Leedy et al. . | |
| 5,064,407 | 11/1991 | Peiffer . | |

Primary Examiner—Mark Rosenbaum
Assistant Examiner—Frances Chin
Attorney, Agent, or Firm—Gifford, Groh, Sprinkle, Patmore and Anderson

[57] ABSTRACT

A granular, biodegradable carrier made from a naturally occurring cellulose material such as corncobs, wood shavings or saw dust, rice hulls, peanut shells and pecan shells. A maximum density cellulose carrier product is produced in a wide variety of granule size ranges by the process of reducing the cellulose material to produce an intermediate pulverulent product, compressing the intermediate pulverulent product to produce pellets, shearing the pellets to produce the granular product, and classifying the granules to the desired size range. Critical control of a moisture addition to the intermediate pulverulent product before it is compressed or pelletized along with selective tempering of the pulverulent product before compression yields a maximum density pellet and a maximum density granular product.

18 Claims, 1 Drawing Sheet

CELLULOSIC CARRIER

BACKGROUND OF THE INVENTION

1. Field of the Invention

This invention relates to biodegradable carriers. More particularly, this invention relates to cellulosic carriers and methods of producing these carriers. The cellulosic carriers of this invention are used primarily for pesticides such as herbicides, insecticides, larvacides, rodenticides and diluents for biological agents.

2. State of the Art

It is well known that cellulose materials are good absorbents, and their use is desirable because they are biodegradable. Cellulose materials such as wood shavings or sawdust, rice hulls, corncobs, pecan shells and peanut shells can be densified by a compacting or a pelletizing process. When the final product is to be used as an absorbent, lower density and higher surface area is desirable. U.S. Pat. Nos. 5,062,954 and 5,064,407, both assigned to The Andersons of Maumee, Ohio, the present assignee, set forth processes for making absorbent products from these materials with corncobs being a preferred material.

Approximately 60% of a corncob is made up of hard woody ring or grit. Corncob grit granules have long been used for a wide variety of pesticide carriers. A good listing of some 37 pesticides by their primary name and also various trade names, which pesticides have been formulated on granular grit carrier, is presented in Table 140 of the publication PHYSICAL PROPERTIES, CHEMICAL PROPERTIES, AND USES OF THE ANDERSONS' CORNCOB PRODUCTS published by The Andersons of Maumee, Ohio. For example, diazinon is currently being used in the eradication of fire ants. Another well known pesticide is known as Dursban ®.

It is also known that the lighter corncob components, which include coarse chaff, fine chaff and pith which constitute about 40% of the corncob by weight, tends to have a higher release rate than the hard woody ring when used as a carrier. This fact is utilized in the teachings of U.S. Pat. No. 4,563,344 assigned to The Andersons. This patent teaches making an agglomerated carrier having a quicker releasing component and a slower releasing component of the soft corncob components and the hard corncob components respectively which are impregnated with different pesticides which are to be released at different rates.

There has been no attempt in the art to produce a dense cellulose carrier having a high resistance to attrition in a granular product in a variety of size ranges.

SUMMARY OF THE INVENTION

The present invention provides a cost effective process for making a high density granular cellulose carrier having a high resistance to attrition. It is known that the effectiveness of solid form pesticides is dependent not only on the active ingredient but also on the inert or carrier ingredient. If the carrier does not effectively release the active ingredient, the active ingredient will never reach its intended target. Therefore, the shape and density of the carrier is important in order to attain the appropriate ballistics to insure uniform distribution whether it be distributed via airplane, helicopter or lawn spreader, but with a minimum carry over to preclude unintended dispersion.

The process of this invention involves the following steps:

A) Reducing a naturally occurring cellulose material to an intermediate pulverulent product.

B) Compressing the intermediate pulverulent product under conditions to yield an intermediate product of compressed bodies having a maximum density, the conditions including:

1) Adding moisture to the intermediate pulverulent product to raise the moisture content to between 16.5 and 18% water.

2) Adding a binder to the intermediate pulverulent product in the amount of 0 to 2% binder.

3) Compressing the intermediate pulverulent product to produce an intermediate product of compressed bodies having a nominal diameter of 3/16" or greater.

C) Fragmenting the intermediate product of compressed bodies under conditions to yield a maximum percentage of granules within a desired size range. This fragmenting is accomplished by a shearing process, which when combined with the moisture control yields an intermediate product of compressed bodies having a minimum friableness hence yielding a minimum of undersized fines.

D) The granules are classified to produce a granular product of granules having a given screen size range.

It has been found that it is desirable or necessary, particularly with a lighter component corncob material to at times temper the moistened feed stock in the range of 3 to 60 minutes. This is preferably accomplished by adding only a portion of the water in an initial stage for example a range of 3 to 6% water is added initially and the feed stock allowed to temper. In the case of lighter component corncob material at about 8% moisture content, this range of moisture addition has been found to be optimum between 4 to 5% initial water addition. After the tempering period has elapsed, additional water preferably in the form of both water and steam is added to raise the moisture content of the mixture to between 16.5 and 18% water.

Generally with a lighter component corncob feed stock there is no need to add a binder. With a wood chip or sawdust cellulose feed stock a binder is preferably used, and calcium lignosulfonate made from tree bark has been found to be a good binder for a wood carrier product. It has also been found that a wood cellulose material does not improve with a tempering step so that the entire moisture addition to between 16.5 and 18% moisture content addition can be made at one time.

The compressing step is preferably accomplished by pelletizing the intermediate pulverulent product by passage through a die yielding an intermediate pellet product having a nominal diameter between 3/16" and 5/16".

Of the 39.7% of the cob which makes up the lighter corncob components, typically 84.9% is coarse chaff, 10.3% is fine chaff and 4.8% is pith. In the initial processing of the corncob, the cob is partially broken up in shelling, crushing, hammermilling and drying which separates the largest percentage of coarse chaff from the cob. Further grinding and otherwise pulverizing the corncob to separate the hard woody ring yields the largest percentage of fine chaff and pith. When the percentage of coarse chaff is proportioned to the amount of fine lighter corncob material, the density of the intermediate product of compressed bodies can be controlled to between 32 and 45 lbs/ft$^3$. This yields a corresponding density of the final granular product from between 22 and 35 lbs/ft$^3$.

In the fragmenting step the intermediate pellet product is sheared by passing between pairs of spaced parallel break rolls. A LePage cut is used with one roll having circumferentially spaced longitudinally extending cutters and the other roll having longitudinally spaced circumferential extending cutters. In a preferred form of the invention for a corncob material, three pairs of break rolls are used, each successive pair having more cutters per inch and each successive pair being spaced closer together.

DESCRIPTION OF THE GRAPHS

FIG. 1 is a graph which displays the relationship between pellet density and moisture level of the material being pelletized; and FIG. 2 is a graph which displays the relationship between pellet density and the make up of the lighter corncob components being pelletized.

DETAILED DESCRIPTION OF THE PRESENTLY PREFERRED EMBODIMENT

In a preferred embodiment of this invention, corn is first shelled or stripped off the cob, and the cob in this process is broken into ¼" to 3" chunks and moved through a dryer. Screening and aspiration at the sheller and dryer removes most of the coarse chaff component of the corncob which represents 85% of the lighter corncob components. As the corncob is further reduced or comminuted by grinding rolls and hammer mills, the lighter chaff material is separated by air classification and the heavier, harder woody ring is removed by air and screening. The lighter chaff material includes the fine chaff or beeswing which constitutes approximately 10% of the lighter corncob material and the pith which constitutes approximately 5%. The coarse chaff and fine chaff and pith are proportioned along with optional return of the fines from a final classification step to make up the pulverulent material feed stock. U.S. Pat. No. 4,053,112, assigned to The Andersons sets forth the apparatus and method for separating the lighter chaff and pith from the woody ring corncob components.

The light pith is largely a fine powder which passes through a 30 mesh screen. The chaff has long strands which can be retained on a number 8 or larger screen. Some hard woody ring material remains unseparated from the chaff and pith so that the composition of the pulverulent material and final granular material is in the range of 91-96% chaff, 4% pith and 0-5% woody ring.

Figure 1:
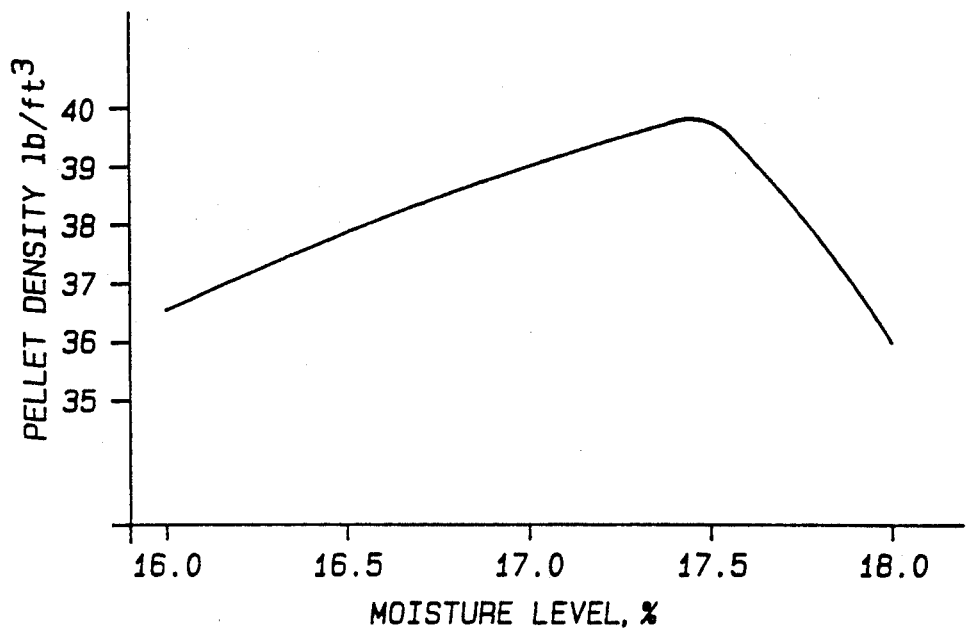

It has been found that adding a controlled amount of water to the pulverulent material is critical to making a compressed body or pellet having a maximum density for the material used. This is true of various mixtures of coarse and fine corncob chaff as seen in FIG. 1 for a given coarse and fine mixture as well as the other cellulose materials mentioned above such as wood and peanut shells. This critical range is from 16.0 to 18% with an optimum maximum density occurring at approximately 17.5% as seen in FIG. 1. With a maximum density there is a minimum friableness which in turn produces, during the shearing and classification steps, less fine material which is below the desired product range size. This also produces a product which is less likely to break down by attrition during subsequent handling.

In many cases, the entire moisture addition to bring the total water content to between 16.0 and 18%, preferably 17.5%, can be made at the entrance to the pellet mill. Also preferably, a portion of this moisture addition is in the form of steam to add lubricity to the pulverulent product for passage through the pellet mill die. However, in the case of a lighter corncob component cellulose material, it has been found necessary during certain times or seasons to add only a portion of water to the intermediate pulverulent product feed stock upstream of the pellet mill in order to allow tempering time for the water to interact with the feed stock. In these cases, 3-6% water is added to the feed stock in a holding bin immediately upstream of the pellet mill. The resident time in the bin can be controlled between 3 to 60 minutes to provide the tempering. It has been found in most cases that the desired consistency for maximum density can be achieved with an initial addition of 4-5% water and a tempering time of 20 minutes. When this tempering step is used, the additional moisture in the form of water and steam is added at the entrance to the pellet mill bringing the total water content up to 16.5 to 18% water.

While the conditions requiring the tempering step are not fully understood, the need for using tempering will be readily recognized when, despite total moisture control of the feed stock, the intermediate pulverulent product will not form coherent firm compact bodies or pellets. In a like manner the need for adding a binder to the feed stock will be apparent from the inability to form firm pellets. For example, with a preferred cellulose material being wood, most commonly pine or poplar, a binder is necessary. With wood, up to 2% calcium lignosulfonate binder addition has been found adequate to achieve maximum density along with the critical 16.0 to 18% total moisture content.

In any event, with a controlled optimum water addition of approximately 17.5%, maximum density of the pellet is achieved in the pelletizing process for many given cellulose materials. FIG. 1 shows the relationship between moisture content and pellet density for a feed stock having approximately 85% coarse chaff and the balance fine chaff and pith. The density of the granular product follows the same curve of density versus moisture content so that providing a maximum density in the pellet will also produce a corresponding maximum density in the final granular product.

Figure 2:
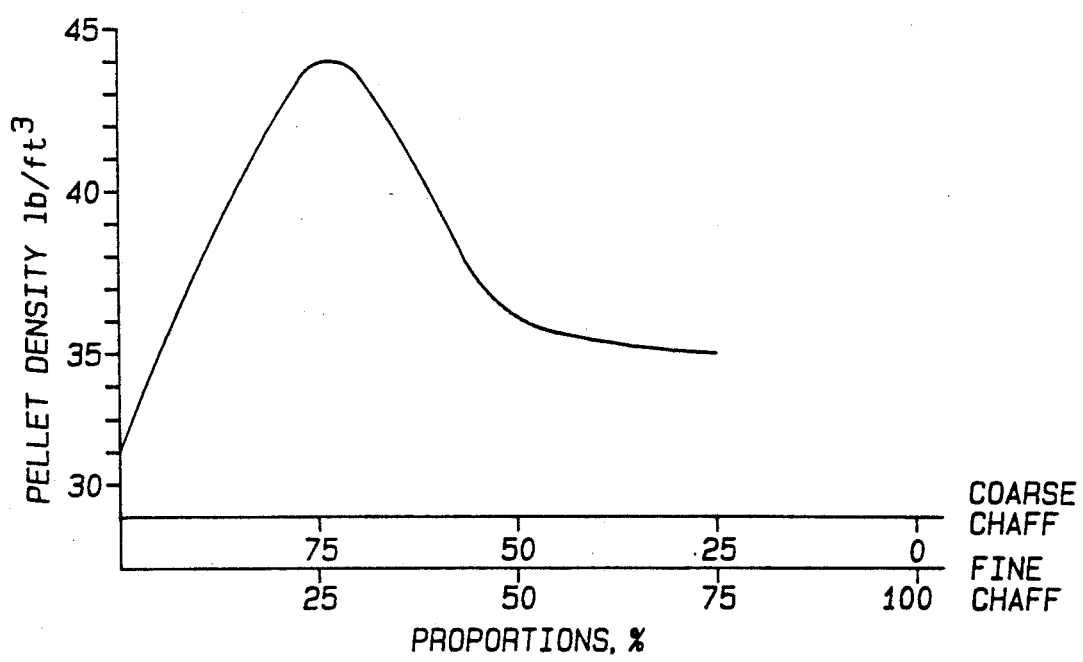

FIG. 2 shows the relationship between proportion of coarse chaff to fine chaff that is used as feed stock with pellet density. It can be seen that when the coarse chaff constitutes approximately three quarters of the total feed stock, a maximum density of approximately 45 lbs/ft.$^3$ can be achieved. Different densities for different end products can be controlled by controlling this mixture of coarse to fine chaff as indicated in FIG. 2.

The compression or compaction process to produce the intermediate compressed bodies for the invention, which has proven to be both very efficient and effective, is pelletizing. Sprout, Waldron & Company, Inc. of Muncy, Pa. manufactures a number of pellet mills suitable for this process. Optimum die opening size lies in the range of 3/16 to 5/16" diameter.

It has also been found important in producing the granular cellulose carrier product of this invention to fragment the intermediate pellet product by a shearing action as opposed to a crumbling or crushing action. This shearing action is accomplished by passing the intermediate pellet product between a pair of spaced break rolls having, one longitudinally extending cutting edges and the other having circumferentially extending cutting edge in what is known as a LePage cut. Each of the pair of break rolls have an equal number of cutting edges, between 10 and 14 per inch of roll circumference. We have found that a 9" diameter roll with this cutting edge spacing produces a very satisfactory product.

It is also been determined that to produce a granular cellulose carrier product from the lighter corncob components starting with a pellet of 3/16 to ¼" diameter that maximum yield and minimum attrition loss of fines occurs by the use of three successive pairs of break rolls to produce a product with a size range between 10-mesh and 60-mesh (number 10 and number 60 screen), with 1240 one of the preferred size ranges. The first two digits of the four digit size designation number indicates the standard screen size through which the final product passes, and the second two digits of the size designation number indicates the standard screen size on which the product is retained. Thus a 1240 product would pass a through a number 12 screen and be retained on a number 40 screen.

With a 3/16" diameter pellet, the first pair of break rolls preferably has 10 cutters per inch and the two rolls are spaced apart a distance of 0.050 to 0.125". The second pair of break rolls has 12 cutters per inch, and the rolls are spaced apart 0.010 to 0.025". The third pair of break rolls 14 cutters per inch and will be spaced apart a distance of 0.003 to 0.015". For a specific final granule size, for example, 1240, the first set of rolls would be preferably set apart approximately 0.080", the second pair of break rolls is preferably set approximately apart 0.015", and the third set of break rolls is preferably set apart approximately 0.007".

Each pair of break rolls is operated with the roll having circumferentially extending cutters rotating at a speed of 200–600 rpm, and the roll with longitudinally extending cutters operated at a higher speed at a ratio of approximately 1 ½ times the lower speed.

If a ¼" pellet is being used, the first set of break rolls would be opened up a little to accommodate the larger size.

In the classification step, the granules from the shearing step are screened through the appropriate larger number screen, and are retained on the lower number screen. For example, with the 1240 product mentioned above, the granules would be screened through a number 12 screen and retained on a number 40 screen. The fines passing through the number 40 screen can be returned to become part of the fine chaff input, and the granules retained on the larger screen can be returned to the coarse or fine feed stock depending upon the particular size of the larger screen.

With the roll spacing set forth above of nominally 0.080", 0.015" and 0.007", a typical output from the third break roll would be 20.3% remaining on a number 10 screen, 20.5% remaining on a number 12 screen, 18.1% remaining a number 14 screen, 25.6% remaining on a number 20 screen, 6.6% remaining on a number 30 screen, 3.6% remaining on a number 40 screen and 5.3% passing through a number 40 screen. When these granules from the third break roll are classified for a final 1240 product, 0.6% remain on a 10 and 12 screen, 13.4% will remain on a number 14 screen, 49.6% will remain on a number 20 screen, 20.2% will remain on a number 30 screen, 13.2% will remain on a number 40 screen, and 3.0% will pass through a number 40 screen. The oversize output of 20.3% remaining on a number 10 screen and the 20.5% remaining on the number 12 screen can be passed through a hammermill where it will be reduced largely to the desired 1240 size range with a small amount of fine passing through a number 40 screen. This further 1240 product will be added to the 1240 product obtained directly from the third break roll. In this fashion a high total yield of the 1240 product is attained with a minimum of −40 fines.

Referring again to FIG. 1, it can be seen that a maximum density cellulosic material pellet can be produced when the moisture level of the intermediate pulverulent product being pelletized is maintained between 16.0 and 18.0%, preferably as close to 17.5% as possible.

Referring to FIG. 2, it can be seen that for a lighter corncob component cellulose material, that the maximum pellet density can be regulated between 32 to 45 lbs/ft$^3$ by controlling the amount of coarse in portion to the amount of fine chaff in the intermediate pulverulent product which is used as a feed stock to the pellet mill.

The release rate of a material on a carrier is determined primarily by the carrier used rather than the density of the carrier. It is estimated that 80% of the release rate is determined by the carrier and perhaps 20% of the release rate is determined by the carrier density.

The carrier of this invention is being used for a diazinon insecticide in the treatment of fire ants. Tests conducted with 5% diazinon on the softer chaff and pith components of a corncob, and the grit or hard woody ring corncob component carrier and on peanut hulls with a granular product having a 1440 size range shows a release rate of the chaff and pith lighter corncob component product to be three times the rate of the grit corncob component and the peanut hull cellulose carrier. In the case of fire ants, the release rate should be as rapid as possible for a desired "instant kill". This would indicate that the chaff and pith corncob component carrier should be used. It provides for a larger amount of insecticide to be released at a given time without using a larger amount of the insecticide itself. This also can result in the use of less active ingredients on this carrier in some instances.

We claim:

1. A process for producing a biodegradable carrier comprising the following steps:
   a) reducing a naturally occurring cellulose material to an intermediate pulverulent product;
   b) compressing the intermediate pulverulent product under conditions to yield an intermediate product of compressed bodies having a maximum density, which conditions include:
      1) adding moisture to said intermediate pulverulent product to raise the moisture content thereof to between 16.0 and 18% water;
      2) adding a binder to said intermediate pulverulent product in the amount of 0 to 2% binder;
      3) compressing the intermediate pulverulent product after steps b) 1) and 2) to produce an intermediate product of compressed bodies having a nominal diameter of at least 3/16" ;
   c) fragmenting said intermediate product of compressed bodies under conditions to yield a maximum percentage of granules within a desired size range, said fragmenting being accomplished by a shearing process, wherein the moisture control in step b) 1) yields an intermediate product of compressed bodies having minimum friableness in step b) 3) so that the shearing process of this step c) yields a minimum of undersized fines; and d) classifying said granules from step c) to produce a granular product of granules having a given screen size range.

2. The process according to claim 1 wherein in step b) 1) moisture is added to the intermediate pulverulent product in an amount which is less than the amount to raise the moisture content to between 16.0 to 18% water, the moistened intermediate pulverulent product is allowed to temper between 3 to 60 minutes, and additional moisture is added to the intermediate pulverulent product to raise the moisture content to between 16.0 and 18% water.

3. The process according to claim 2 wherein the naturally occurring cellulose material in step a) consists essentially of corncob components.

4. The process according to claim 3 wherein the corncob components in step a) are the lighter chaff portions of the cob consisting essentially of the chaff with minor amounts of pith along with a minor amount of the heavier portion of the cob consisting essentially of woody ring.

5. The process according to claim 4 wherein the corncob components in step a) consist essentially of 91-96% chaff, 1-4% pith and 0-5% woody ring.

6. The process according to claim 4 wherein no binder is added to the intermediate pulverulent product.

7. The process according to claim 1 wherein the moisture added in step b) 1) raises the moisture content to approximately 17.5%.

8. The process according to claim 1 wherein during fragmenting step c), the intermediate product of compressed bodies is passed between a pair break rolls which effect the shearing.

9. The process according to claim 8 and providing said break rolls with 10 to 14 cutting edges per inch and spacing said rolls apart a distance of 0.003 to 0.125".

10. The process according to claim 1 wherein the cellulose material is wood, and the intermediate pulverulent product of step a) is sawdust.

11. The process according to claim 10 wherein in step b) 2) calcium lignosulfonate is used as a binder.

12. A process for producing a biodegradable carrier comprising the following steps:
a) reducing and separating the chaff and pith lighter components of corncobs to produce an intermediate pulverulent product;
b) compressing the intermediate pulverulent product under conditions to yield an intermediate product of compressed bodies having a maximum density, which conditions include:
1) adding 3 to 6% water to said intermediate pulverulent product;
2) tempering the intermediate pulverulent product of step 1) between 3 and 60 minutes;
3) adding moisture to said intermediate pulverulent product of step 2) to raise the moisture content to 16.0 to 18% water;
4) pelletizing the intermediate pulverulent product of step 3) by passage through a die to produce an intermediate pellet product having a nominal diameter of at least 3/16";
c) fragmenting said intermediate pellet product under conditions to yield a maximum percentage of granules within a desired size range, said fragmenting being accomplished by a shearing as the intermediate pellet product is passed between break rolls, wherein the moisture control in step b) 1), 2) and 3) yields an intermediate pellet product having minimum friableness in step b) 4) so that the fragmenting process of this step c) yields a minimum of undersized fines; and
d) classifying said granules from step c) to produce a granular product of said granules having a given screen size range.

13. The process according to claim 12 wherein in step b) 3) the moisture is added in the form of water and steam.

14. The process according to claim 13 and providing the break rolls used to shear the intermediate pellet product in step c) with 10 to 14 cutters per inch and spacing said rolls apart 0.003 to 0.125".

15. The process according to claim 14 wherein in step b) 1) 4 to 5% water is added and in the fragmenting step c), the intermediate pellet product is sheared by passing the intermediate pellet product through three pairs of breaks rolls, the first pair of break rolls being provided with 10 cutters per inch and being spaced apart 0.050 to 0.125", the second pair of break rolls being provided with 12 cutters per inch and being spaced apart 0.010 to 0.025", and the third pair of break rolls being provided with 14 cutters per inch and being spaced apart 0.003 to 0.015".

16. The process according to claim 15 wherein in step b) 1) 4 to 5% water is added and said first set of break rolls are spaced apart approximately 0.080", said second set of break rolls are set apart approximately 0.015" and said third set of break rolls are set apart approximately 0.007".

17. The process according to claim 13 wherein the moisture added in step b) 3) raises the moisture content to approximately 17.5%.

18. The process according to claim 12 wherein step a) includes shelling, crushing, hammermilling and drying the corncobs to produce a first amount of coarse chaff and proportioning said first amount to a second amount of fine lighter corncob material in order to control the density of said intermediate pellet product from step b) 4) to between 32 and 45 lb/ft$^3$ thereby controlling the density of the granular product from step d) to between 22 and 35 lb/ft$^3$.

* * * * *